US012624380B2

(12) United States Patent
Kim et al.

(10) Patent No.: US 12,624,380 B2
(45) Date of Patent: May 12, 2026

(54) MICRO-OBJECT EXTRACTION METHOD USING DIFFUSIOPHORESIS, AND MICRO-OBJECT IDENTIFICATION METHOD USING SAME

(71) Applicant: UNIST(ULSAN NATIONAL INSTITUTE OF SCIENCE AND TECHNOLOGY), Ulsan (KR)

(72) Inventors: Taesung Kim, Ulsan (KR); Dogyeong Ha, Ulsan (KR)

(73) Assignee: UNIST(ULSAN NATIONAL INSTITUTE OF SCIENCE AND TECHNOLOGY), Ulsan (KR)

( * ) Notice: Subject to any disclaimer, the term of this patent is extended or adjusted under 35 U.S.C. 154(b) by 1052 days.

(21) Appl. No.: 17/771,829

(22) PCT Filed: Nov. 5, 2020

(86) PCT No.: PCT/KR2020/015374
§ 371 (c)(1),
(2) Date: Apr. 26, 2022

(87) PCT Pub. No.: WO2021/101135
PCT Pub. Date: May 27, 2021

(65) Prior Publication Data
US 2022/0372541 A1     Nov. 24, 2022

(30) Foreign Application Priority Data

Nov. 19, 2019     (KR) ........................ 10-2019-0148551

(51) Int. Cl.
*C12Q 1/04*     (2006.01)
*B01L 3/00*     (2006.01)
(Continued)

(52) U.S. Cl.
CPC .......... *C12Q 1/24* (2013.01); *B01L 3/502761* (2013.01); *C12Q 1/04* (2013.01);
(Continued)

(58) Field of Classification Search
CPC ......... B01L 2200/0647; B01L 2200/16; B01L 2300/0896; B01L 2400/0421;
(Continued)

(56) References Cited

U.S. PATENT DOCUMENTS

2002/0006670 A1     1/2002  Wu et al.

FOREIGN PATENT DOCUMENTS

KR     10-0738071 B1     7/2007
KR     10-1716302 B1     3/2017

OTHER PUBLICATIONS

Ha et al., Dynamic Transport Control of Colloidal Particles by Repeatable Active Switching of Solute Gradients. ACS Nano 2019, 13, 12939-12948 (Year: 2019).*

(Continued)

*Primary Examiner* — Lydia Edwards
(74) *Attorney, Agent, or Firm* — Revolution IP, PLLC

(57) ABSTRACT

The present invention relates to a micro-object extraction method using diffusiophoresis enabling collection and extraction of micro-objects by using the concentration difference of a solution including the micro-objects to be extracted, and a micro-object identification method using same, wherein the present invention has the following advantages: desired micro-objects can be easily extracted only with a simple device by using diffusiophoresis; the collection and extraction of micro-objects can be easily controlled by changing the type of solution injected into a micro-channel; and energy usage is efficient by using self-powered energy by diffusiophoresis without separate external power required for extracting micro-objects.

9 Claims, 8 Drawing Sheets

(51) Int. Cl.
    *B01L 99/00*        (2010.01)
    *C12Q 1/24*        (2006.01)

(52) U.S. Cl.
    CPC ... *B01L 2200/0647* (2013.01); *B01L 2200/16*
        (2013.01); *B01L 2300/0896* (2013.01); *B01L*
        *2400/0421* (2013.01); *B01L 2400/0472*
        (2013.01)

(58) Field of Classification Search
    CPC ....... B01L 2400/0472; B01L 3/502761; B01L
        2300/0864; B01L 2300/0867; B01L
        2300/088; B01L 2300/168; B01L
        3/502707; B01L 3/50273; C12Q 1/04;
        C12Q 1/24; G01N 35/08; G01N 35/085
    See application file for complete search history.

(56) References Cited

OTHER PUBLICATIONS

International Search Report for PCT/KR2020/015374 mailed Feb.
15, 2021 from Korean Intellectual Property Office.

* cited by examiner (a)

(b)

(a)

(b)

(a)

(b)

MICRO-OBJECT EXTRACTION METHOD USING DIFFUSIOPHORESIS, AND MICRO-OBJECT IDENTIFICATION METHOD USING SAME

TECHNICAL FIELD

The present invention relates to a micro-object extraction method using diffusiophoresis and a micro-object identification method using the method, and more particularly, to a micro-object extraction method using diffusiophoresis enabling collection and extraction of micro-objects by using the concentration difference of a solution including the micro-objects to be extracted, and a micro-object identification method using the method.

BACKGROUND ART

Point-of-care testing means testing that can be performed in real time without pretreatment of a clinical specimen not in a medical institution but at a site and can be used in diagnosis and treatment, and can be applied to various fields such as disease prevention, disease clinical diagnosis, treatment effect decision, and the like. In point-of-care testing, a perishable material to be tested, such as blood, is immediately diagnosed at a site and thus, there is an advantage of preventing the risk of deterioration or contamination or the like. In particular, such point-of-care testing is essential in Africa or underdeveloped nations of Asia that is difficult to get help from medical institutions.

In order for point-of-care testing to be effective, a technology for concentrating a test target material, a technology for separating the test target material from foreign substances, and a technology for extracting the test target material are required. In addition, simplification of an electrical device or a mechanical device is required for a device for point-of-care testing. However, existing technologies take a long time to concentrate the test target material, and equipment therefor is also complicated.

DETAILED DESCRIPTION OF THE INVENTION

Technical Problem

The present invention provides a micro-object extraction method using diffusiophoresis enabling collection and extraction of micro-objects by using the concentration difference of a solution including the micro-objects to be extracted, and a micro-object identification method using the method.

Technical solution

According to an aspect of the present invention, there is provided a micro-object extraction method using diffusiophoresis, the micro-object extraction method including preparing a micro-object collection and extraction apparatus including a first microchannel and a second microchannel being spaced apart from each other, a collection channel extending from the second microchannel to the first microchannel, and a connection nanochannel connecting the first microchannel to the collection channel, collecting micro-objects into the collection channel by chemiphoresis caused by a concentration difference between the first solution and the second solution and by electrophoresis caused by a diffusivity difference of the first solution by flowing a first solution having a first concentration into the first microchannel and flowing a second solution having a lower second concentration than the first concentration and the micro-objects together into the second microchannel, and extracting the micro-objects from the collection channel to the second microchannel by chemiphoresis caused by a concentration difference between the third solution and the fourth solution and by electrophoresis caused by a diffusivity difference of the third solution by flowing a third solution having a third concentration into the first microchannel and flowing a fourth solution having a lower fourth concentration than the third concentration into the second microchannel.

According to another aspect of the present invention, there is provided a micro-object collection and extraction identification method using diffusiophoresis, the micro-object collection and extraction identification method including preparing a micro-object collection and extraction apparatus including a first microchannel and a second microchannel being spaced apart from each other, a collection channel extending from the second microchannel to the first microchannel, and a connection nanochannel connecting the first microchannel to the collection channel, collecting micro-objects into the collection channel by chemiphoresis caused by a concentration difference between the first solution and the second solution and by electrophoresis caused by a diffusivity difference of the first solution by flowing a first solution having a first concentration into the first microchannel and flowing a second solution having a lower second concentration than the first concentration and genetically-modified micro-organisms together into the second microchannel, reacting the micro-organisms collected in the collection channel with a chemical material by flowing the chemical material causing a chemical reaction with the genetically-modified micro-organisms into the first microchannel, and extracting the micro-objects from the collection channel to the second microchannel by chemiphoresis caused by a concentration difference between the third solution and the fourth solution and by electrophoresis caused by a diffusivity difference of the third solution by flowing a third solution having a third concentration into the first microchannel and flowing a fourth solution having a lower fourth concentration than the third concentration into the second microchannel.

Effects of the invention

A micro-object extraction method using diffusiophoresis according to the present invention has the following effects.

First, desired micro-objects can be easily extracted only with a simple device by using diffusionphoresis.

Second, the collection and extraction of micro-objects can be easily controlled by changing the type of solution injected into a microchannel.

Third, energy usage is efficient by using self-powered energy by diffusiophoresis without separate external power required for extracting micro-objects.

MODE OF THE INVENTION

Hereinafter, the present invention will be described in detail by describing an exemplary embodiment of the present invention with reference to the accompanying drawings.

Figure 1:
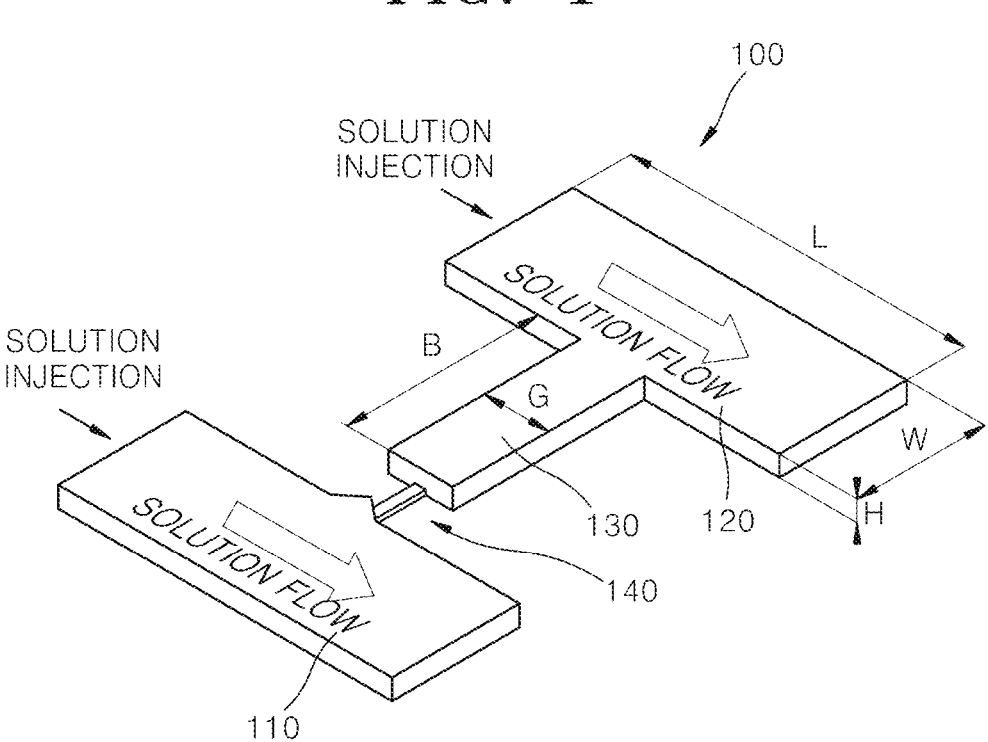
FIG. 1 is a perspective view illustrating an apparatus used in a micro-object extraction method using diffusionphoresis according to an embodiment of the present invention.

FIG. 1 illustrates a micro-object extraction apparatus 100 using diffusiophoresis used in a micro-object extraction method using diffusiophoresis according to an embodiment of the present invention. Referring to FIG. 1, the micro-object extraction apparatus 100 using diffusiophoresis includes a first microchannel 110, a second microchannel 120, a collection channel 130, and a connection nanochannel 140. In the micro-object extraction apparatus 100 using diffusiophoresis, the first microchannel 110, the second microchannel 120, the collection channel 130, and the connection nanochannel 140 may be formed on a main body, such as polymer or the like. Materials for forming the main body may include all materials capable of forming a channel.

The micro-object extraction apparatus 100 using diffusiophoresis performs diffusiophoresis, and this diffusiophoresis is generated by the sum of chemiphoresis (CP) and electrophoresis (EP). The chemiphoresis (CP) is performed in a direction toward a high concentration, and the electrophoresis (EP) is performed according to a diffusivity difference parameter 1β by the following equation. The diffusivity difference parameter means a diffusivity difference between cations and anions that are present in a solution and is a nondimensionalized parameter.

$$\beta=(D_+-D_-)/(D_++D_-)$$

Here, β is a diffusivity difference parameter, $D_+$ is a diffusivity coefficient of cations in the solution, and $D_-$ is a diffusivity coefficient of anions in the solution.

A first solution having a first concentration or a third solution having a third concentration flows through the first microchannel 110. The first microchannel 110 has a width W of 200 μm and a height H of 10 μm. However, the present invention is not limited thereto, and the width of the first microchannel 110 may be changed into 100 μm to 300 μm, and the height of the first microchannel 110 may be changed in the range of 5 μm to 20 μm. The first microchannel 110 has a relatively large length than the width or height. That is, the first microchannel 110 has a length L of 5 mm. However, the present invention is not limited thereto, but the length of the first microchannel 110 may be changed in the range of 1 mm to 20 mm.

The second microchannel 120 is disposed to be spaced apart from the first microchannel 110. A second solution having a second concentration lower than the first concentration and a fourth solution having a fourth concentration lower than the third concentration flow through the second microchannel 120. Also, micro-objects also flow together with the second solution through the second microchannel 120. In the present embodiment, Escherichia coli is used as the micro-objects. However, the present invention is not limited thereto, and the micro-objects may be changed into micro-organisms except for Escherichia coli or other micro-particles. In the present embodiment, Escherichia coli in a genetically modified state is used to express a fluorescent signal by itself when it encounters acyl homoserine lactone.

And in the present embodiment, the second microchannel 120 has the same width, the same height and the same length as those of the first microchannel 110. However, the present invention is not limited thereto, but the width, the height, and the length of the second microchannel 110 may be changed differently from those of the first microchannel 110.

The first solution, the second solution, the third solution, and the fourth solution include a solute that separates into cations and anions. The same type or different types of the first solution and the second solution may be used. And the same type or different types of the third solution and the fourth solution may also be used. Different types from the types of the third solution and the fourth solution are used as the first solution and the second solution. In the present embodiment, a solution in which sodium chloride (NaCl) is added to M9 minimal medium, is used as the first solution, and M9 minimal medium described above is used as the second solution. And a case where a solution in which potassium acetate (K-acetate) is added to M9 minimal medium, is used as the third solution and M9 minimal medium described above is used as the fourth solution, will be exemplified. Of course, any types of the first solution and the second solution and any types of the third solution and the fourth solution may be changed. That is, sodium chloride aqueous solutions may be used as all of the first solution and the second solution, and potassium acetate aqueous solutions are used as all of the third solution and the fourth solution.

The collection channel 130 is formed to extend from the second microchannel 120 to the first microchannel 110. The second solution having the second concentration and the fourth solution having the fourth concentration may flow through the collection channel 130, and Escherichia coli may be collected or extracted by the collection channel 130. In the collection channel 130, a convection motion may be prevented, and a concentration gradient of a solution may be formed in a lengthwise direction based on a center.

In the present embodiment, the collection channel 130 has an extension length B of 200 μm and a width G of 50 μm. However, the present invention is not limited thereto, and the length of the collection channel 130 may be changed in the range of 100 μm to 300 μm, and the width of the collection channel 130 may be changed in the range of 30 μm to 70 μm. The collection channel 130 has the same height of 10 μm as the height of the first microchannel 110 and the height of the second microchannel 120. However, the present invention is not limited thereto, and the height of the collection channel 130 may be changed in the range of 5 μm to 20 μm.

The connection nanochannel 140 connects the first microchannel 110 to the collection channel 130. The connection nanochannel 140 has a cross-sectional area through which Escherichia coli cannot pass. However, the connection nanochannel 140 has a cross-sectional area through which the first solution and the third solution flowing through the first microchannel 110 pass. That is, the connection nanochannel 140 has a cross-sectional area through which cations and anions constituting the first solution and the third solution pass. Also, the connection nanochannel 140 has a cross-sectional area through which the second solution and the fourth solution flowing through the second microchannel 120 pass. That is, the connection nanochannel 140 has a cross-sectional area through which cations and anions constituting the second solution and the fourth solution pass.

In order to guarantee more excellent connection, a portion of the first microchannel 110 connected to the connection nanochannel 140 has a protruding shape. In the present embodiment, the protruding shape is formed in a triangular structure. Of course, any protruding shape may be changed.

The connection nanochannel 140 has the length of 5 μm, the width of 2 μm, and the height of 180 nm. However, the present invention is not limited thereto, and the length of the connection nanochannel 140 may be changed in the range of 1 μm to 10 μm, the width of the connection nanochannel 140 may be changed in the range of 1 μm to 3 μm, and the height of the connection nanochannel 140 may be changed in the range of 100 nm to 300 nm.

The connection nanochannel 140 may be formed based on crack. The connection nanochannel 140 may be formed in the following illustrative manner. First, a photomask having patterns with at least one notch formed therein is prepared in the center. When the photomask is prepared, an operation in which a photolithography process is performed on a base material coated with a photosensitive material by using the photomask to fabricate a first mold block and crack is formed on the first mold block, is performed. After the first mold block is prepared, an operation in which a second mold having an embossing shape is fabricated by using the first mold block and embossing protrusions and a crack protrusion are formed, is performed. After the fabrication of the second mold is completed, a microchannel block is fabricated by supplying a resin based on the second mold, and the connection nanochannel 140 is formed on the microchannel block. In the cracking process, the photosensitive material is cured by irradiated light during the photolithography process, and crack starts being generated from a notch portion of a through hole formed while an exposure operation and a development operation are performed. While light is irradiated onto the photosensitive material, stress is concentrated on the notch portion. The photosensitive material is cured when light is irradiated onto the photosensitive material by cross linking to be bonded to each other. However, when a stress concentration energy of the notch portion is greater than energy of cross linking, crack is generated from the notch portion.

Figure 2:
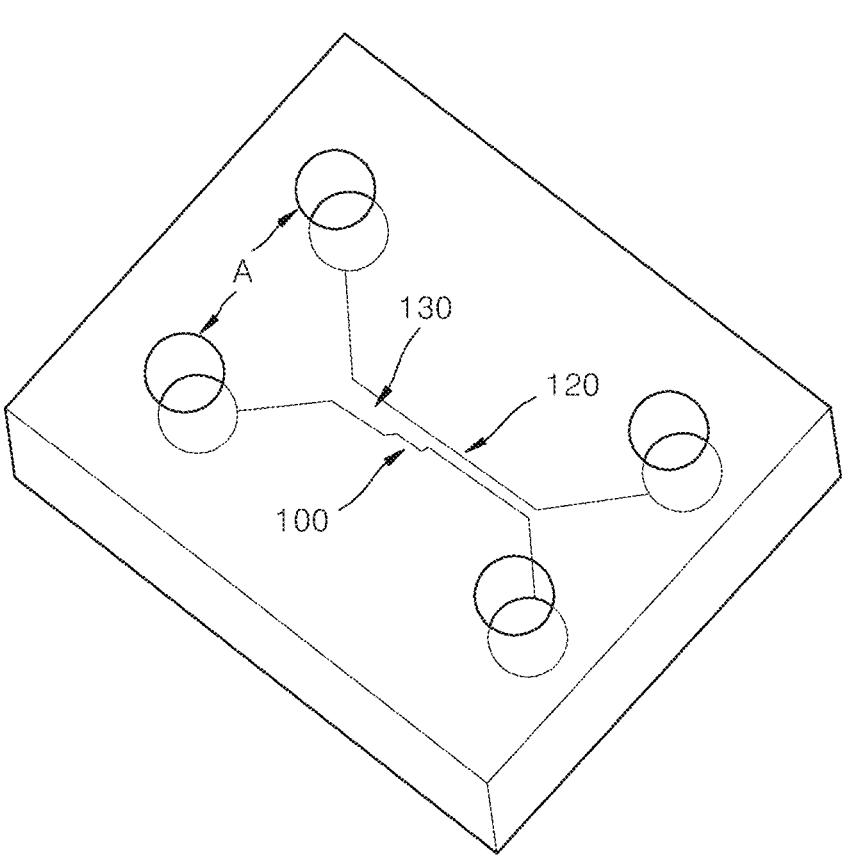
FIG. 2 is a photo showing the apparatus used in a micro-object extraction method using diffusiophoresis shown in FIG. 1.

FIG. 2 is a photo showing the micro-object extraction apparatus 100 using diffusiophoresis shown in FIG. 1. Referring to FIG. 2, the connection nanochannel 140 is also formed in addition to the first microchannel 110, the second microchannel 120, and the collection channel 130. Each of the first solution, the second solution, the third solution, and the fourth solution may be injected into an inlet A. Through a simple method of changing a solution to be injected into the inlet, the physical and chemical environment of the connection nanochannel 130 may be rapidly and dynamically changed.

Figure 3:
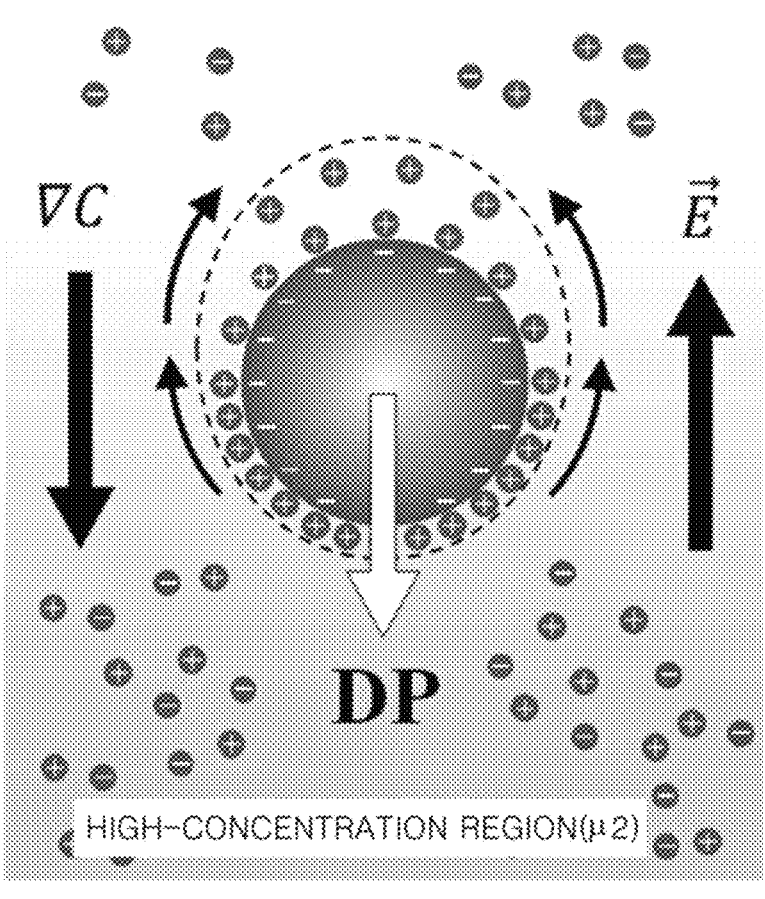
FIG. 3 is a schematic diagram for describing the principle of diffusiophoresis applied to the micro-object extraction method using diffusiophoresis shown in FIG. 1.
Figure 4:
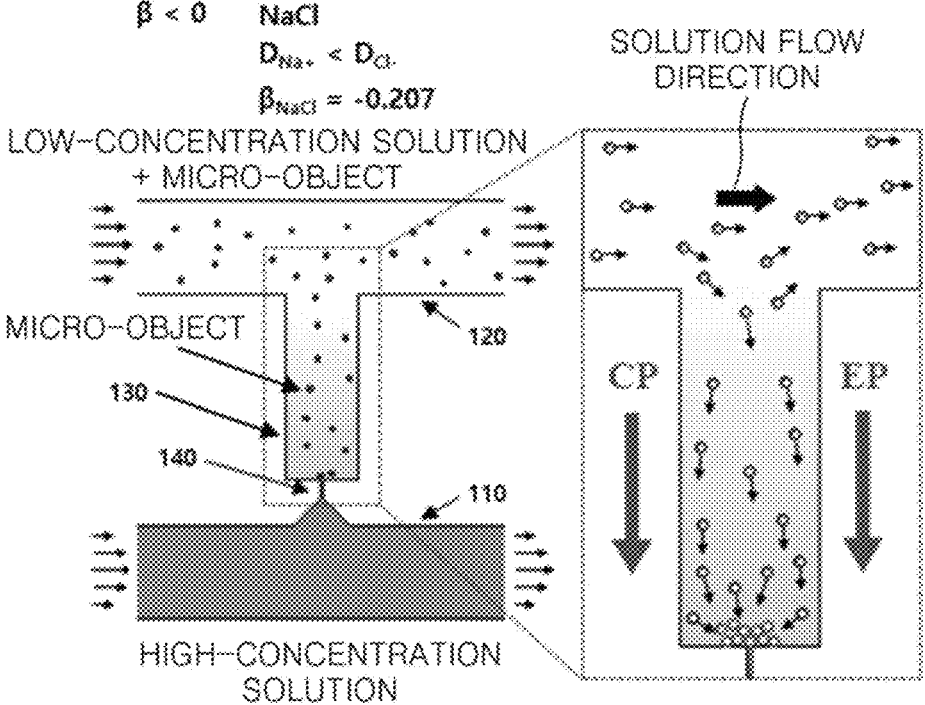
FIG. 4 is a schematic diagram for describing an operation of collecting micro-objects in a collection channel in the micro-object extraction method using diffusiophoresis shown in FIG. 1.
Figure 5:
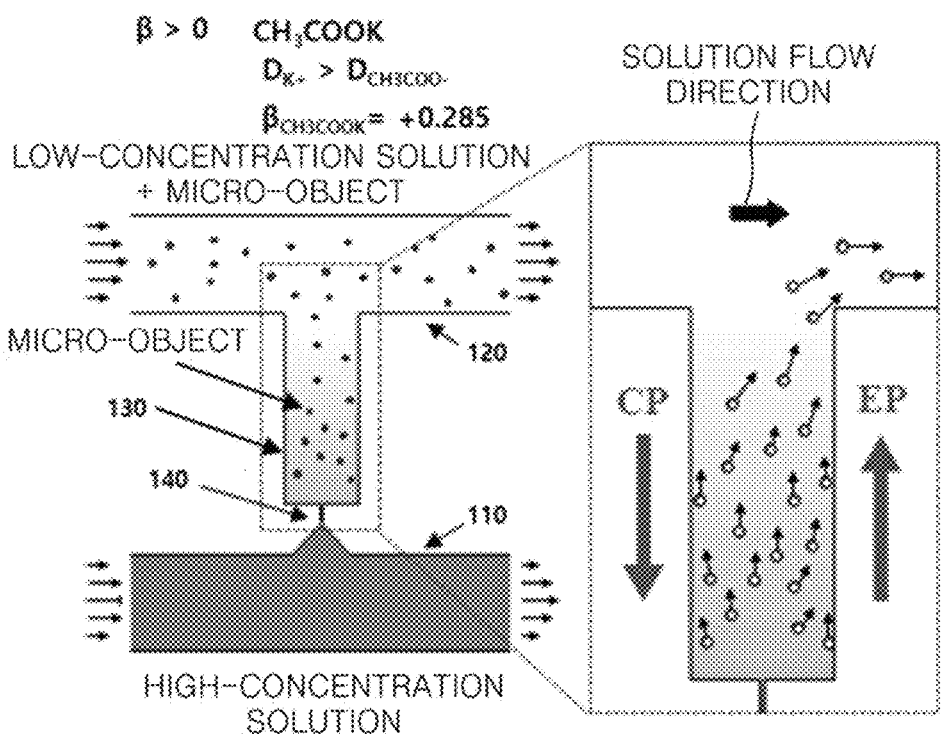
FIG. 5 is a schematic diagram for describing an operation of extracting the micro-objects from the collection channel in the micro-object extraction method using diffusiophoresis shown in FIG. 1.

FIGS. 3 through 5 are schematic diagrams for describing the principle of diffusiophoresis applied to the micro-object extraction method using diffusiophoresis shown in FIG. 1. Referring to FIG. 3, micro-objects are mixed in an NaCl aqueous solution having a high concentration ($\mu$1) region and a low concentration ($\mu$2) region. The micro-objects are negatively charged, are arranged in the center, and the high-concentration region of the NaCl aqueous solution is disposed at lower sides of the micro-objects, and the low-concentration region of the NaCl aqueous solution is disposed at upper sides of the micro-objects.

Hereinafter, the chemiphoresis will be described. A concentration difference $\nabla C$ between the high concentration and the low concentration of the NaCl aqueous solution is generated. Diffusion occurs due to the concentration difference, and in detail, water that is a solvent migrates from the high concentration to the low concentration by diffusion. Contrary to the migration of the solvent, the micro-objects undergo chemiphoresis in a downward direction from the low-concentration region on the upper side to the high-concentration region on the lower side.

Hereinafter, the electrophoresis will be described. In the NaCl aqueous solution, NaCl separates into cations of Na$^+$ and anions of Cl$^-$. Because the micro-objects are negatively charged, the cations are attracted into the micro-objects by an electrical attractive force, and the anions are away from the micro-objects by an electrical repulsive force. In case of NaCl, the diffusivity $D_+$ of the cations is less than the diffusivity $D_-$ of the anions. Thus, a greater amount of anions than the amount of the cations migrate with higher velocity than the velocity of the cations from the high-concentration region to the low-concentration region, i.e., in an upward direction. Due to the difference of relative migration, more cations are present on lower sides of the micro-objects so that an electrical attractive force in a downward direction increases, and more anions are present on upper sides of the micro-objects so that an electrical repulsive force in the downward direction increases. That is, due to the difference of relative migration of the cations and the anions, the micro-objects undergo electrophoresis in the downward direction from the low-concentration region on the upper side to the high-concentration region on the lower side. For reference, an electrical field E formed by the cations and the anions has a direction from the lower side where the cations are relatively large, to the upper side where the anions are relatively large.

Contrary to this, when the diffusivity of the cations is greater than the diffusivity of the anions, for example, in case of potassium acetate (K-acetate) of FIG. 5, the cations migrate faster than the anions and thus, the electrophoresis occurs in the upward direction.

Also, when the micro-objects are positively charged, the micro-objects migrate in an opposite manner to the above description. That is, when the diffusivity of the cations is less than the diffusivity of the anions, the micro-objects migrate in the upward direction, and when the diffusivity of the cations is greater than the diffusivity of the anions, the micro-objects migrate in the downward direction.

FIG. 4 is a schematic diagram for describing an operation of collecting micro-objects in the collection channel 130 in the micro-object extraction method using diffusiophoresis shown in FIG. 1. Referring to FIG. 4, M9 minimal medium including several ions is used as the first solution and the second solution so as to maintain the vital activity of

*Escherichia coli.* In this case, NaCl 9 mM is contained in M9 1× solution. In order to maintain the minimal vital activity of *Escherichia coli* and maximize the concentration difference of NaCl between the first solution and the second solution, both the first solution and the second solution are diluted by 100 times to make M9 0.01φ. The NaCl concentration of the first solution is adjusted to 2 M, and only M9 0.01φsolution is purely used as the second solution. Thus, 90 μM is contained in the second solution. *Escherichia coli* is used as the micro-objects flowing through the second microchannel 120 and collected in the collection channel 130.

A high-concentration NaCl aqueous solution flows through the first microchannel 110, and a low-concentration NaCl aqueous solution and negatively-charged *Escherichia coli* flow through the second microchannel 120. The flow direction of a solution in the first microchannel 110 and the flow direction of a solution in the second microchannel 120 are illustrated the same. However, this is just illustrative, and the flow direction of the solution in the first microchannel 110 and the flow direction of the solution in the second microchannel 120 may be opposite to each other.

Because the solution concentration of the first microchannel 110 and the solution concentration of the second microchannel 120 are different from each other, the high-concentration solution of the first microchannel 110 flows into the collection channel 130 through the connection nanochannel 140. Thus, the concentration is reduced in the order of the first microchannel 110, the collection channel 130, and the second microchannel 120.

In case of sodium chloride (NaCl), the diffusivity $D_{Na+}$ of cations Na$^+$ is less than the diffusivity $D_{Cl-}$ of anions Cl$^-$. Thus, a diffusivity difference parameter 1β is a negative value, −0.207. According to the principle of diffusiophoresis described with reference to FIG. 3, *Escherichia coli* flowing in the second microchannel 120 is collected in the collection channel 130. That is, *Escherichia coli* migrates by chemiphoresis (CP) generated by a concentration difference and electrophoresis (EP) generated by a negative diffusivity difference parameter. The direction of the chemiphoresis and the direction of the electrophoresis are the same, and specifically, in a direction from the second microchannel 120 to the first microchannel 110 within the collection channel 130. Also, *Escherichia coli* does not pass through the connection nanochannel 140 and thus does not migrate into the first microchannel 110. Thus, *Escherichia coli* is collected from a region adjacent to the first microchannel 110 within the collection channel 130.

FIG. 5 is a schematic diagram for describing an operation of extracting the micro-objects from the collection channel 130 in the micro-object extraction method using diffusiophoresis shown in FIG. 1. Referring to FIG. 5, the third solution that is a high-concentration solution flowing through the third microchannel 110 is formed in such a way that potassium acetate (K-acetate) concentration in the M9 0.01× solution is 100 mM, in a similar manner to a manner of the first solution. The fourth solution that is a low-concentration solution flowing through the second microchannel 120 is formed in such a way that potassium acetate (K-acetate) is not contained in the M9 0.01× solution. The flow direction of the solution in the first microchannel 110 and the flow direction of the solution in the second microchannel 120 are illustrated the same. However, this is illustrative, and the flow direction of the solution in the first microchannel 110 and the flow direction of the solution in the second microchannel 120 may be opposite to each other. Because the concentration of the first microchannel 110 and the concentration of the second microchannel 120 are different from each other, the high-concentration solution of the first microchannel 110 flows into the collection channel 130 through the connection nanochannel 140. Thus, the concentration is reduced in the order of the first microchannel 110, the collection channel 130, and the second microchannel 120.

In case of K-acetate (CH$_3$COOK), the diffusivity $D_{K+}$ of cations K$^+$ is greater than the diffusivity $D_{CH3COO-}$ of anions CH$_3$COO$^-$. Thus, the diffusivity difference parameter β is a positive value, +0.285. According to the principle of diffusiophoresis described with reference to FIG. 3, Escherichia coli collected in the collection channel 130 is extracted into the second microchannel 120. That is, *Escherichia coli* migrates by chemiphoresis (CP) generated by a concentration difference and electrophoresis (EP) generated by a positive diffusivity difference parameter. The direction of the chemiphoresis (CP) and the direction of the electrophoresis (EP) are opposite to each other. The chemiphoresis, like in the case of FIG. 4, is in a direction from the second microchannel 120 to the first microchannel 110 within the collection channel 130. On the other hand, the electrophoresis is in a direction from the first microchannel 110 to the second microchannel 120 within the collection channel 130. When the force of the electrophoresis is greater than the force of the chemiphoresis, the micro-objects are extracted from the collection channel 130 into the second microchannel 120.

Figure 6:
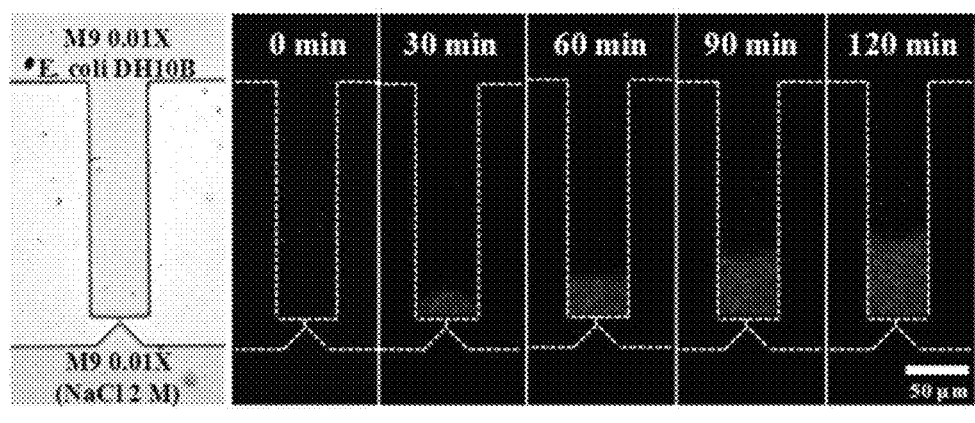
FIG. 6 is a photo and a graph showing a state in which the micro-objects are collected in the collection channel in the micro-object extraction method using diffusiophoresis shown in FIG. 1.
Figure 6:
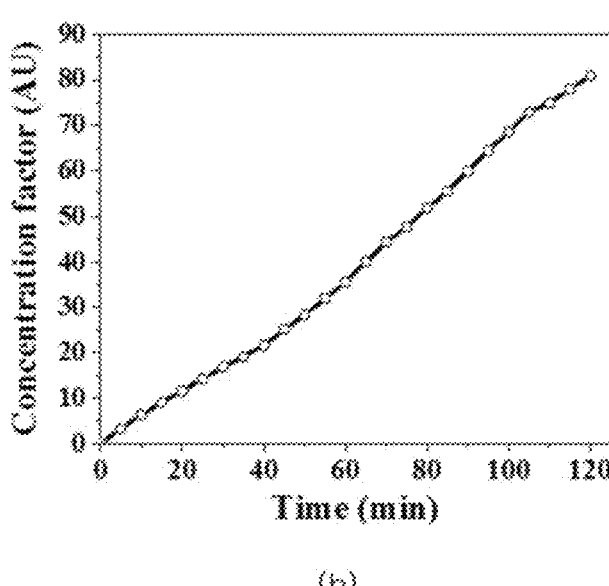

Hereinafter, the micro-object collection and extraction process by using the micro-object extraction method using diffusiophoresis shown in FIG. 1 will be described by using experimental photos and graphs with reference to FIGS. 6 through 8. FIG. 6 illustrates a process in which the micro-objects are collected in the collection channel 130 in the process of FIG. 4. *Escherichia coli* collected in the collection channel 130 is indicated in green. When the flow of the NaCl solution starts in the first microchannel 110 and the second microchannel 120, respectively, *Escherichia coli* is collected from a region adjacent to the connection nanochannel 140 within the collection channel 130 and is accumulated so that the volume of *Escherichia coli* is gradually increased. After about 120 minutes has elapsed, *Escherichia coli* may be collected to the height of about ⅓ of the collection channel 130. In this case, it can be seen that *Escherichia coli* increases at an almost constant rate over time.

When the collection channel 130 has the extension length of 200 μm, the width of 50 μm and the height of 10 μm, the volume of the collection channel 130 is 100,000 μm$^3$. When *Escherichia coli* is 0.05% w/v, 100,000×0.0005=50 particles. The integration velocity is calculated as about 20,000 particles/hr, and this represents the integration velocity of about 5 particles/sec.

Figure 7:
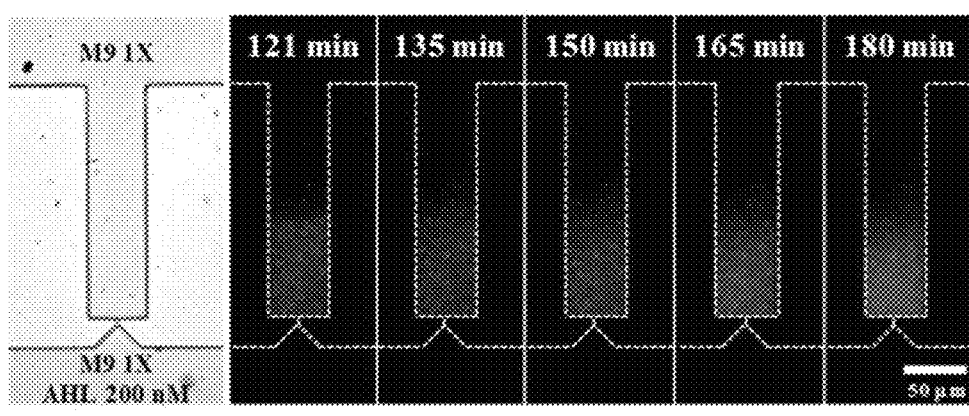
FIG. 7 is a photo and a graph showing a state in which a specific chemical material is injected into the collection channel so as to visually identify the micro-objects collected in the collection channel in the micro-object extraction method using diffusiophoresis shown in FIG. 1.
Figure 7:
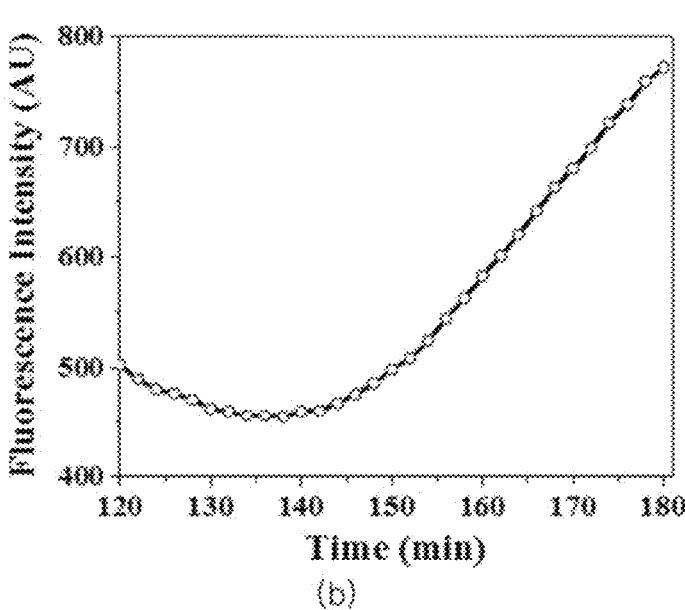

FIG. 7 is a photo and a graph showing a state in which a specific chemical material is injected into the collection channel so as to visually identify the micro-objects collected in the collection channel in the micro-object extraction method using diffusiophoresis shown in FIG. 1. In this case, in order to match the vital activity of *Escherichia coli* used as the micro-objects to a universal condition, a M9 1× solution is used as the third solution injected into the first microchannel 110 and the fourth solution injected into the second microchannel 120. According to this, it can be seen that there is a difference between the color of a fluorescent signal at 121 minutes and the color of a fluorescent signal at 180 minutes. That is, it can be seen that from 121 minutes to 180 minutes over time, the fluorescent signals by the micro-objects show a tendency to become darker from the bottom approximately. This is because when genetically-modified *Escherichia coli*, which is the micro-objects used in this experiment, encounters an acyl homoserine lactone (AHL) and emits a fluorescent signal, the acyl homoserine lactone increases over time, and the acyl homoserine lactone is sequentially encountered from *Escherichia coli* collected in the lower part of the collection channel 130. It can be seen that the intensity of the fluorescent signal is 500 AU at 120 minutes at which the acyl homoserine lactone starts to be injected, whereas the intensity of the fluorescent signal is approximately 800 AU after 180 minutes have elapsed, which is a 1.6-fold increase.

Figure 8:
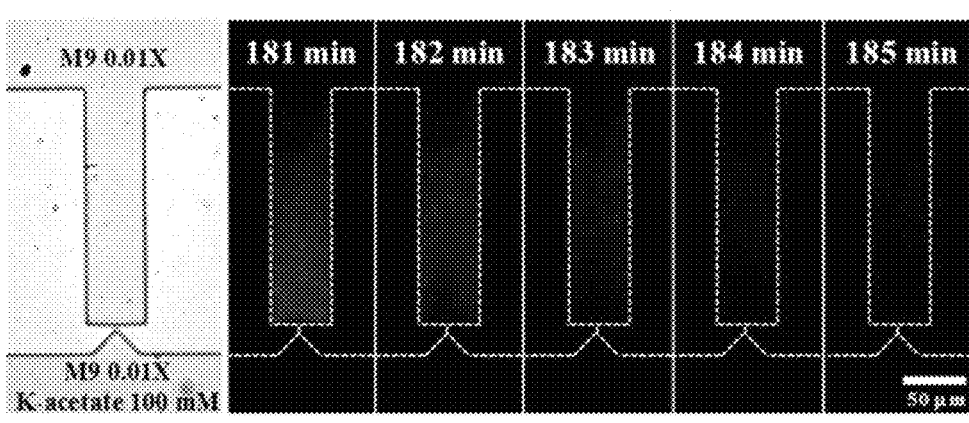
FIG. 8 is a photo and a graph showing a state in which the micro-objects are extracted from the collection channel in the micro-object extraction method using diffusiophoresis shown in FIG. 1.

FIG. 8 is a photo and a graph showing a state in which the micro-objects are extracted from the collection channel 130 in the micro-object extraction method using diffusiophoresis shown in FIG. 1. Referring to FIG. 8, *Escherichia coli* collected in the collection channel 130 is indicated in green. When the flow of high-concentration K-acetate starts from the first microchannel 110 and the flow of low-concentration K-acetate starts from the second microchannel 120, *Escherichia coli* migrates from the collection channel 130 to the second microchannel 120. That is, *Escherichia coli* is extracted from the collection channel 130. It can be seen that about 80% of *Escherichia coli* is extracted at 185 minutes at which extraction starts and 5 minutes have elapsed, and about 95% or more of *Escherichia coli* is extracted at 190 minutes at which 10 minutes have elapsed. That is, it can be seen that *Escherichia coli* may be rapidly extracted in a short time. For reference, in order to prevent Escherichia coli from being unwantedly confined in the second microchannel 130, about 0.02% of a nonionic surfactant such as Pluronic F-127 may be mixed in solutions at the first microchannel 110 and the second microchannel 120 and may flow.

A process of identifying whether micro-objects are collected, based on the above experimental procedure and a process of extracting the micro-object is summarized as follows, first, a first solution having the first concentration flows in the first microchannel 110, and a second solution having a lower second concentration than the first concentration and *Escherichia coli* that are the micro-objects required for identification and extraction flow together in the second microchannel 120. At this time, negatively-charged *Escherichia coli* is used, and a NaCl aqueous solution having a negative (−) diffusivity is used as the first solution and the second solution. In this way, *Escherichia coli* is collected into the collection channel 130 by chemiphoresis caused by the concentration difference between the first solution and the second solution and electrophoresis caused by the diffusivity difference of the first solution. Because *Escherichia coli* collected in the collection channel 130 is not visually identified, *Escherichia coli* that is previously genetically modified to express a fluorescent signal by encountering a specific chemical material, for example, acyl homoserine lactone, is used.

Next, 200 nM of acyl homoserine lactone flows through the first microchannel 110. Acyl homoserine lactone flows through the first microchannel 110 and flows into the collection channel 130 through the connection nanochannel 140. Thus, *Escherichia coli* collected in the lower part of the collection channel 130 expresses a fluorescent signal by encountering acyl homoserine lactone. Thus, the amount of *Escherichia coli* collected in the collection channel 130 may be visually identified. In this case, acyl homoserine lactone flows continuously so that the intensity of the fluorescent signal can be increased.

Next, the third solution having the third concentration flows in the first microchannel 110, and a fourth solution having a lower fourth concentration than the third concentration flows through the second microchannel 120. In this case, a K- acetate aqueous solution having a positive (+) diffusivity is used as the third solution and the fourth solution. In this way, *Escherichia coli* is extracted from the collection channel 130 in a direction toward the second microchannel 120 by chemiphoresis caused by the concentration difference between the third solution and the fourth solution and electrophoresis caused by the diffusivity difference of the third solution. Because even in this case, *Escherichia coli* expresses a fluorescent signal, it can be visually easily seen from the intensity of the fluorescent signal in the collection channel 130 how much *Escherichia coli* is extracted.

While the present invention has been particularly shown and described with reference to exemplary embodiments thereof, it will be understood by those of ordinary skill in the art that various changes in form and details may be made therein without departing from the spirit and scope of the present invention as defined by the following claims.

INDUSTRIAL APPLICABILITY

According to the present invention, a method of extracting required micro-objects easily with only a simple device by using diffusiophoresis can be provided.

The invention claimed is:

1. A micro-object extraction method using diffusiophoresis, the micro-object extraction method comprising:

preparing a micro-object collection and extraction apparatus including a first microchannel and a second microchannel being spaced apart from each other, a collection channel extending from the second microchannel to the first microchannel, and a connection nanochannel connecting the first microchannel to the collection channel;

collecting micro-objects into the collection channel by chemiphoresis caused by a concentration difference between a first solution and a second solution and by electrophoresis caused by a diffusivity difference of the first solution by flowing the first solution having a first concentration into the first microchannel and flowing the second solution having a lower second concentration than the first concentration and the micro-objects together into the second microchannel; and extracting the micro-objects from the collection channel to the second microchannel by chemiphoresis caused by a concentration difference between the third solution and the fourth solution and by electrophoresis caused by a diffusivity difference of the third solution by flowing a third solution having a third concentration into the first microchannel and flowing a fourth solution having a lower fourth concentration than the third concentration into the second microchannel.

2. The micro-object extraction method of claim 1, wherein, in the collecting of the micro-objects, the micro-objects comprise negatively (−) charged micro-organisms or particles, and the diffusivity difference of the first solution has a negative (−) value.

3. The micro-object extraction method of claim 1, wherein, in the extracting of the micro-objects, the micro-objects comprise negatively (−) charged micro-organisms or particles, and the diffusivity difference of the third solution has a positive (+) value.

4. The micro-object extraction method of claim 1, wherein, in the collecting of the micro-objects, the micro-objects comprise positively (+) charged micro-organisms or particles, and the diffusivity difference of the first solution has a positive (+) value.

5. The micro-object extraction method of claim 1, wherein, in the extracting of the micro-objects, the micro-objects comprise positively (+) charged micro-organisms or particles, and the diffusivity difference of the third solution has a negative (−) value.

6. The micro-object extraction method of claim 1, wherein the first solution and the second solution are of same type of solutions having different concentrations.

7. The micro-object extraction method of claim 6, wherein the first solution and the second solution are sodium chloride (NaCl) aqueous solutions.

8. The micro-object extraction method of claim 1, wherein the third solution and the fourth solution are of same type of solutions having different concentrations.

9. The micro-object extraction method of claim 8, wherein the third solution and the fourth solution are potassium acetate (K-acetate) aqueous solutions.

* * * * *